United States Patent
Blank et al.

(10) Patent No.: US 12,043,641 B2
(45) Date of Patent: Jul. 23, 2024

(54) MINIMALLY-INVASIVE CONTINUOUS CLINICAL MONITORING OF SMALL MOLECULES WITH ANALYTICAL ACCURACY

(71) Applicant: TECHNION RESEARCH & DEVELOPMENT FOUNDATION LIMITED, Haifa (IL)

(72) Inventors: Aharon Blank, Haifa (IL); Jens Anders, Ulm (DE); José Vidal Gancedo, Madrid (ES); Vega Lloveras Monserrat, Madrid (ES)

(73) Assignee: TECHNION RESEARCH & DEVELOPMENT FOUNDATION LIMITED, Haifa (IL)

( * ) Notice: Subject to any disclaimer, the term of this patent is extended or adjusted under 35 U.S.C. 154(b) by 120 days.

(21) Appl. No.: 17/777,684

(22) PCT Filed: Nov. 18, 2020

(86) PCT No.: PCT/IL2020/051197
§ 371 (c)(1),
(2) Date: May 18, 2022

(87) PCT Pub. No.: WO2021/100042
PCT Pub. Date: May 27, 2021

(65) Prior Publication Data
US 2023/0026678 A1     Jan. 26, 2023

Related U.S. Application Data

(60) Provisional application No. 62/936,689, filed on Nov. 18, 2019.

(51) Int. Cl.
*C07F 9/58* (2006.01)
*G01N 24/10* (2006.01)

(52) U.S. Cl.
CPC ............... *C07F 9/58* (2013.01); *G01N 24/10* (2013.01)

(58) Field of Classification Search
CPC ....... C07F 9/58; C07F 9/65815; G01N 24/10; A61F 2/82; A61F 2250/0002; C07D 211/94; G01R 33/60
See application file for complete search history.

(56) References Cited

U.S. PATENT DOCUMENTS
2011/0165087 A1     7/2011   Kao et al.

FOREIGN PATENT DOCUMENTS
DE      102010008417 A1 *   8/2011  ........... C07D 257/02
WO      1995028966 A1      11/1995
(Continued)

OTHER PUBLICATIONS

Machine translation of DE-102010008417-A1 (Year: 2011).*
(Continued)

*Primary Examiner* — G. M. A Hyder
(74) *Attorney, Agent, or Firm* — The Roy Gross Law Firm, LLC; Roy Gross

(57) ABSTRACT

A dendrimer including a ring core moiety, a paramagnetic group, a linking moiety and a branching moiety for continuously probing and quantifying an analyte is provided together with methods, kits and devices for performing sensitive, accurate and durable measurements.

9 Claims, 4 Drawing Sheets

(56) References Cited

FOREIGN PATENT DOCUMENTS

| WO | 2006049913 | A1 | 5/2006 |
|---|---|---|---|
| WO | 2017190144 | A1 | 11/2017 |

OTHER PUBLICATIONS

Michael J Davies, Detection and characterization of radicals using electron paramagnetic resonance (EPR) spin trapping and related methods, Elsevier, available on line May 19, 2016 (Year: 2016).*
Henke H, Posch S, Brüggemann O, Teasdale I. Polyphosphazene Based Star-Branched and Dendritic Molecular Brushes. Macromol Rapid Commun. May 2016;37(9):769-74. doi: 10.1002/marc. 201600057. Epub Mar. 29, 2016. PMID: 27027404; PMCID: PMC4907350.
Suzen S, Gurer-Orhan H, Saso L. Detection of Reactive Oxygen and Nitrogen Species by Electron Paramagnetic Resonance (EPR) Technique. Molecules. Jan. 21, 2017;22(1):181. doi: 10.3390/molecules22010181. PMID: 28117726; PMCID: PMC6155876.
Zgadzai O, Twig Y, Wolfson H, Ahmad R, Kuppusamy P, Blank A. Electron-Spin-Resonance Dipstick. Anal Chem. Jul. 3, 2018;90(13):7830-7836. doi: 10.1021/acs.analchem.8b00917. Epub Jun. 13, 2018. PMID: 29856211.
Lloveras V, Badetti E, Wurst K, Vidal-Gancedo J. Synthesis, X-Ray Structure, Magnetic Properties, and a Study of Intra/Intermolecular Radical-Radical Interactions of a Triradical TEMPO Compound. Chemphyschem. Oct. 26, 2015;16 (15):3302-7. doi: 10.1002/cphc. 201500462. Epub Aug. 26, 2015. PMID: 26489060.
E. Badetti, V. Lloveras, J. L. Muñoz-Gómez, R. M. Sebastián, A. M. Caminade, J. P. Majoral, J. Veciana, and J. Vidal-Gancedo. Radical Dendrimers: A Family of Five Generations of Phosphorus Dendrimers Functionalized with TEMPO Radicals. Macromolecules 2014 47 (22), 7717-7724 DOI: 10.1021/ma502062q.
E. Badetti, V. Lloveras, K. Wurst, R. M. Sebastián, A. M. Caminade, J. P. Majoral, J. Veciana, and J. Vidal-Gancedo. Synthesis and Structural Characterization of a Dendrimer Model Compound Based on a Cyclotriphosphazene Core with TEMPO Radicals as Substituents. Organic Letters 2013 15 (14), 3490-3493 DOI: 10.1021/ol401017c.
Ke C, Destecroix H, Crump MP, Davis AP. A simple and accessible synthetic lectin for glucose recognition and sensing. Nat Chem. Sep. 2012;4(9):718-23. doi: 10.1038/nchem.1409. Epub Aug. 5, 2012. PMID: 22914192.
Smith, John. (2006). The Pursuit of Noninvasive Glucose: Hunting the Deceitful Turkey.
Burleson, W., & Carrara, S. (Eds.). (2014). Security and Privacy for Implantable Medical Devices. doi:10.1007/978-1-4614-1674-6.
Yang X, Pan X, Blyth J, Lowe CR. Towards the real-time monitoring of glucose in tear fluid: holographic glucose sensors with reduced interference from lactate and pH. Biosens Bioelectron. Jan. 18, 2008;23(6):899-905. doi: 10.1016/j.bios.2007.09.016. Epub Sep. 29, 2007. PMID: 18060763.
Wang, M.J. & Tsai W.-B. Biomaterials in Blood-Contacting Devices: Complications and Solutions. Nova Science Publishers, New York 2010.
Luijf YM, Mader JK, Doll W, Pieber T, Farret A, Place J, Renard E, Bruttomesso D, Filippi A, Avogaro A, Arnolds S, Benesch C, Heinemann L, DeVries JH; AP@home consortium. Accuracy and reliability of continuous glucose monitoring systems: a head-to-head comparison. Diabetes Technol Ther. Aug. 2013;15(8):722-7. doi: 10.1089/dia.2013.0049. Epub May 7, 2013. PMID: 23650900; PMCID: PMC3746288.
Gault, V.A., & McClenaghan, N.H. (2009). Understanding Bioanalytical Chemistry: Principles and Applications.
Soares DP, Law M. Magnetic resonance spectroscopy of the brain: review of metabolites and clinical applications. Clin Radiol. Jan. 2009;64(1):12-21. doi: 10.1016/j.crad.2008.07.002. Epub Aug. 30, 2008. PMID: 19070693.
Dhar V. Big Data and Predictive Analytics in Health Care. Big Data. Sep. 2014;2(3):113-6. doi: 10.1089/big.2014.1525. PMID: 27442491.

Belle A, Thiagarajan R, Soroushmehr SM, Navidi F, Beard DA, Najarian K. Big Data Analytics in Healthcare. Biomed Res Int. 2015;2015:370194. doi: 10.1155/2015/370194. Epub Jul. 2, 2015. PMID: 26229957; PMCID: PMC4503556.
Stoeckel D, Pelton A, Duerig T. Self-expanding nitinol stents: material and design considerations. Eur Radiol. Feb. 2004;14(2):292-301. doi: 10.1007/s00330-003-2022-5. Epub Sep. 3, 2003. PMID: 12955452.
Wolfson, H., Ahmad, R., Twig, Y. et al. A Miniature Electron Spin Resonance Probehead for Transcutaneous Oxygen Monitoring. Appl Magn Reson 45, 955-967 (2014). https://doi.org/10.1007/s00723-014-0593-8.
Woflson, H., Ahmad, R., Twig, Y., Williams, B., & Blank, A. (2015). A Magnetic Resonance Probehead for Evaluating the Level of Ionizing Radiation Absorbed in Human Teeth. Health Physics, 108(3), 326-335. doi: 10.1097/hp.0000000000000187.
Blank, A., Alexandrowicz, G., Muchnik, L., Tidhar, G., Schneiderman, J., Virmani, R. and Golan, E. (2005), Miniature self-contained intravascular magnetic resonance (IVMI) probe for clinical applications. Magn. Reson. Med., 54:105-112. https://doi.org/10.1002/mrm.20537.
C. Chen, P. Seifi and A. Babakhani, "A silicon-based, fully integrated pulse electron paramagnetic resonance system for mm-wave spectroscopy," 2013 IEEE MTT-S International Microwave Symposium Digest (MTT), Seattle, WA, USA, 2013, pp. 1-3, doi: 10.1109/MWSYM.2013.6697730.
Turner, W. J., Xiao, Z., Wu, S., Beck, B. L., Bashirullah, R., & Mareci, T. H. (2010). Digitally controlled µ-chip capacitor array for an implantable multiple frequency coil. In Proc. 18th Annu. Meeting ISMRM (Stockholm, Sweden) (p. 424).
X. Yang and A. Babakhani, "A Single-Chip Electron Paramagnetic Resonance Transceiver in 0.13-µ m SiGe BiCMOS," in IEEE Transactions on Microwave Theory and Techniques, vol. 63, No. 11, pp. 3727-3735, Nov. 2015, doi: 10.1109/ TMTT.2015.2481895.
J. Handwerker, B. Schlecker, U. Wachter, P. Radermacher, M. Ortmanns and J. Anders, "28.2 A 14GHz battery-operated point-of-care ESR spectrometer based on a 0.13µm CMOS ASIC," 2016 IEEE International Solid-State Circuits Conference (ISSCC), San Francisco, CA, USA, 2016, pp. 476-477, doi: 10.1109/ISSCC.2016.7418114.
J. Anders, J. Handwerker, M. Ortmanns and G. Boero, "A fully-integrated detector for NMR microscopy in 0.13µm CMOS," 2013 IEEE Asian Solid-State Circuits Conference (A-SSCC), Singapore, 2013, pp. 437-440, doi: 10.1109/ ASSCC.2013.6691076.
Ferri S, Kojima K, Sode K. Review of glucose oxidases and glucose dehydrogenases: a bird's eye view of glucose sensing enzymes. J Diabetes Sci Technol. Sep. 1, 2011;5(5):1068-76. doi: 10.1177/193229681100500507. PMID: 22027299; PMCID: PMC3208862.
Baron, A. (Apr. 27, 2022). Why is Nitinol Used in Stents?—Kellogg's Research Labs. Kellogg's Research Labs. https://www.kelloggsresearchlabs.com/2020/06/03/why-is-nitinol-used-in-stents/.
Arnaud, J., Audfray, A., & Imberty, A. (2013). Binding sugars: from natural lectins to synthetic receptors and engineered neolectins. Chemical Society Reviews, 42(11), 4798. doi:10.1039/c2cs35435g.
Schmid, C., Haug, C., Heinemann, L., & Freckmann, G. (2013). System Accuracy of Blood Glucose Monitoring Systems: Impact of Use by Patients and Ambient Conditions. Diabetes Technology & Therapeutics, 15(10), 889-896. doi:10.1089/dia.2013.0047.
Surman F, Riedel T, Bruns M, Kostina NY, Sedláková Z, Rodriguez-Emmenegger C. Polymer brushes interfacing blood as a route toward high performance blood contacting devices. Macromol Biosci. May 2015;15(5):636-46. doi: 10.1002/mabi.201400470. Epub Jan. 21, 2015. PMID: 25644402.
Córcoles, E. P., & Boutelle, M. G. (2013). Biosensors and Invasive Monitoring in Clinical Applications. SpringerBriefs in Applied Sciences and Technology. doi:10.1007/978-3-319-00360-3.
Contactless Connectivity. (2013). In Eindhoven University of Technology [Presentation]. 2013 Research Retreat, Netherlands. https://assets.w3.tue.nl/w/fileadmin/content/faculteiten/ee/Onderzoek/Technologische_centra/Centre_for_Wireless_Technology/CWTe_2013_RR_Riezebos-TEConnectivity.pdf.

(56) References Cited

OTHER PUBLICATIONS http://senseonics.com. (Jul. 14, 2015). The Sensor. Senseonics. https://web.archive.org/web/20160119042453/http:/senseonics.com/product/the-sensor.

Bowes WA 3rd, Corke BC, Hulka J. Pulse oximetry: a review of the theory, accuracy, and clinical applications. Obstet Gynecol. Sep. 1989;74(3 Pt 2):541-6. PMID: 2668828.

PCT International Search Report for International Application No. PCT/IL2020/051197, mailed Feb. 11, 2021, 6pp.

PCT International Preliminary Report on Patentability for International Application No. PCT/IL2020/051197, issued May 17, 2022, 7pp.

\* cited by examiner

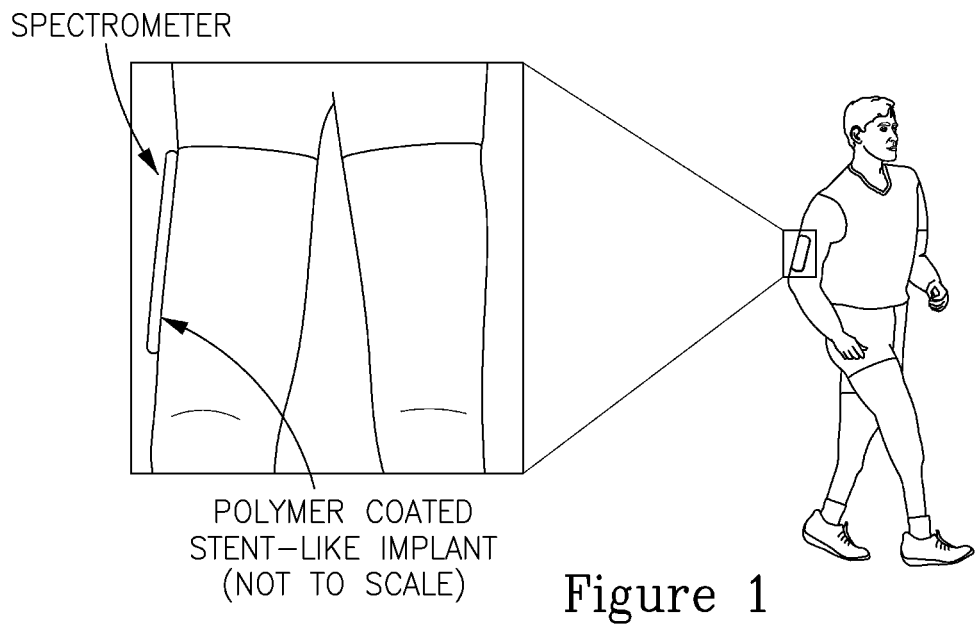
Figure 1
POLYMER COATED STENT-LIKE IMPLANT (NOT TO SCALE)
SPECTROMETER
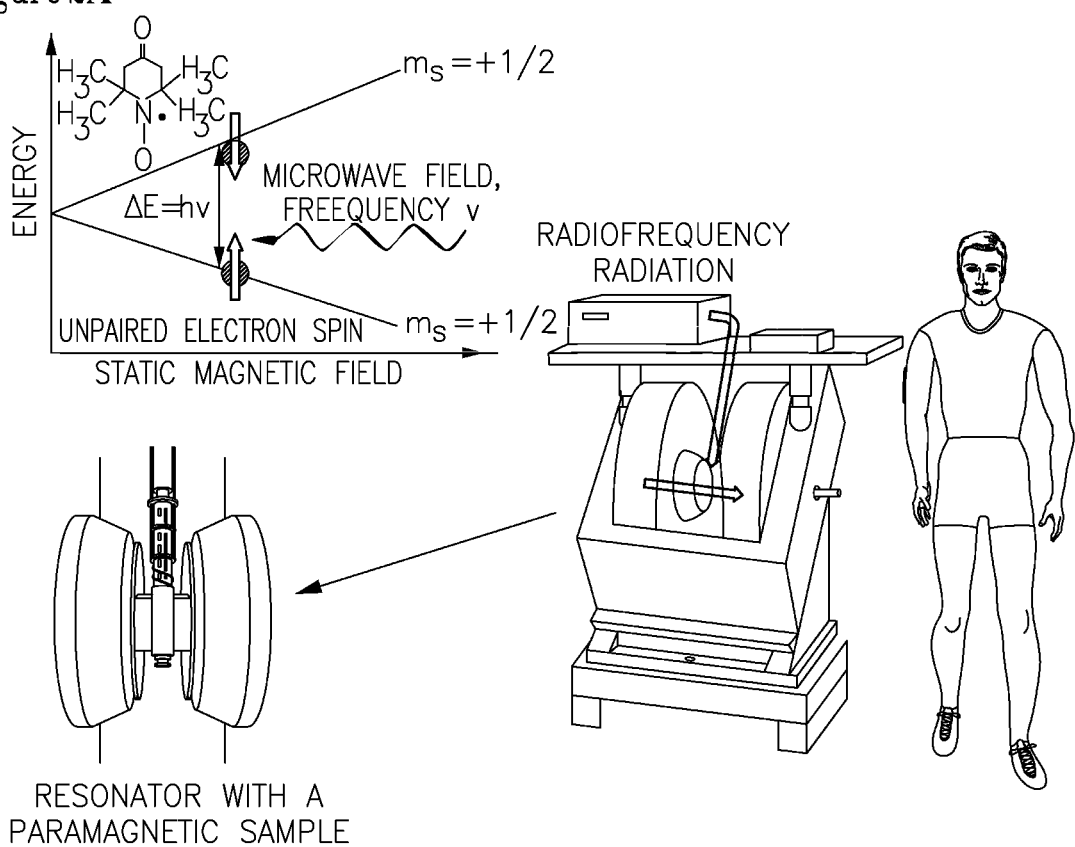
Figure 2A
Figure 2C — RESONATOR WITH A PARAMAGNETIC SAMPLE
Figure 2B

MINIMALLY-INVASIVE CONTINUOUS CLINICAL MONITORING OF SMALL MOLECULES WITH ANALYTICAL ACCURACY

CROSS REFERENCE TO RELATED APPLICATIONS

This application is a National Phase of PCT Patent Application No. PCT/IL2020/051197 having International filing date of Nov. 18, 2020, which claims the benefit of priority under 35 U.S.C. § 119(e) of U.S. Provisional Patent Application No. 62/936,689, filed on Nov. 18, 2019, titled "MINIMALLY-INVASIVE CONTINUOUS CLINICAL MONITORING OF SMALL MOLECULES WITH ANALYTICAL ACCURACY", the contents of which are all incorporated by reference as if fully set forth herein in their entirety.

FIELD OF THE INVENTION

A dendrimer for continuously probing and quantifying an analyte is provided together with methods, kits and devices for performing sensitive, accurate and durable measurements.

BACKGROUND OF THE INVENTION

Sensors for the continuous and accurate monitoring of small molecules in the body, such as glucose, are required technologies in the field of medical devices. The leading approach for small molecules sensing makes use of electrochemical methods using a chemical or an enzyme that reacts with the molecule of interest and generate product that can be detected electrochemically. Electrochemical methods are sensitive but present several drawbacks: a. They do not measure the glucose in the blood but rather work in the subcutaneous interstitial tissue, which negatively affects the device's sensitivity and accuracy. b. Electrochemical sensors exhibit large drifts and require frequent calibrations. c. The enzymes quickly degrade and sensors have to be replaced every 5-14 days at the latest. d. The needle with the enzyme probe must be continuously connected to an instrument or a transmitter outside the body.

In order to improve the life span of continuous glucose-monitoring implants, researchers are currently trying to move away from methods that use exogenous molecules that react with the small molecules of interest (e.g., glucose). This trend has recently led towards methods in which newly synthesized fluorescent molecular with components (e.g., synthetic lectins) that reversibly bind to the molecule of interest and where these binding events are then detected using optical methods. This results in fairly large, full-of-electronics, centimeter-sized implants that cannot be placed in the bloodstream and thus suffer from many of the above-mentioned drawbacks of the subcutaneously-placed electrochemical needles. Furthermore, optical methods are fairly non-specific (meaning that many molecules present fluorescence) and thus the fluorescence signal can be affected by the environment, leading to significant measurement noise over real analyte-to-be-detected concentration values.

One of the reasons for the limited range of functional paramagnetic species available is the relatively high complexity, size and cost of electron spin resonance (ESR) systems needed to detect them (compared to relatively compact fluorescence systems, for example), and their more complex chemistry.

These include a static magnetic field, which orients the magnetic moment of the electron either parallel or antiparallel with respect to its direction, and a microwave radiation, tuned in frequency to the energy difference between the two states which induces transitions that can be detected to characterize the sample.

In classical ESR detection setups, the sample is placed in a microwave resonator, which is excited using an external high-power, high-cost microwave source and discrete electronics. The high static magnetic field, commonly in the 0.1-2 T range, is generated with large, power-hungry electromagnets. Paramagnetic molecules as functional probes their use is far less common than e.g., florescence.

Although recently commercial benchtop and academic prototypes of point-of-care ESR spectrometers have become available, these devices all work in the so-called continuous-wave mode, their size is still in the order of 10s of cm, their weight is several 10s of kgs, their cost is several 10s of k€s, and their power consumption is still in the range of hundreds of Watts.

SUMMARY OF THE INVENTION

This invention, in some embodiments thereof, relates to use of molecular binding approach using paramagnetic tags. Paramagnetic tags may be measured and characterized by ESR spectrometers.

In one embodiment, this invention provides a compound characterized by a dendritic structure, represented by the general Formula I: $W-[B_1]_n^0-[B_2]_m^1-[B_3]_m^2- \ldots [B_g-]_m^{g-1}-[D]^h L^i-G^j$ wherein:
  W is a core moiety (e.g., a ring moiety);
  D comprises a paramagnetic (e.g., free radical) group (e.g., TEMPO);
  L is a G-linking moiety;
  G is a species selected from the group consisting: carbohydrate, cholesterol, urea, creatine, and an ion;
  $B_1, B_2, B_3 \ldots B_g$ are each independently a branching moiety, wherein $B_1, B_2, B_3 \ldots B_g$ together form said dendritic structure;
  n is an integer that equals to 2 to 6,
  g is an integer that ranges from 1 to 10, representing the number of generations of said dendritic structure.
  m is an integer that equals 1, 2, or 3 representing, in each occurrence, the ramification number of each generation;
  h is an integer that ranges from 1 to $n \times m^1 \times m^2 \times \ldots m^{g-1}$, representing the total numbers of D in said dendritic structure;
  i is an integer that ranges from 1 to h, representing the total numbers of L in said dendritic structure, and
  j is an integer that ranges from 0 to i, representing the total numbers of G in said dendritic structure. In one embodiment, G-linking moiety comprises one or more functional groups. In one embodiment, D is a radical. In one embodiment, the core moiety comprises a phosphorus-containing ring.

In another embodiment, the invention further provides a device or a kit, comprising: (a) the compound as described herein; and (b) a unit comprising a compact electron spin resonance spectrometer (e.g., a compact ESR).

In another embodiment, the invention further provides a method of paramagnetically monitoring an amount of a molecule within a composition, the method comprising: contacting the compound of the invention with a composition; and employing an electron spin resonance probe for monitoring the amount of said molecule.

In another embodiment, the invention further provides a method for in-vivo monitoring an amount of a molecule within a bodily fluid or a tissue in a subject, comprising attaching the device or a kit of the invention to the subject, wherein attaching comprises: (a) inserting the compound into the bodily fluid or tissue; and (b) externally coupling the unit to the subject, thereby monitoring an amount of a molecule within a bodily fluid or tissue.

BRIEF DESCRIPTION OF THE DRAWINGS

FIG. 1 is an illustration of a device and a kit for analytical-grade-accuracy minimally-invasive body chemicals measurements. The Unit placed on the arm includes electron spin resonance spectrometer detecting the signal from a paramagnetic molecule that binds to the molecule of interest (e.g., glucose). The paramagnetic molecule is embedded in an implantable stent placed in the blood vessel or tissue. Upon binding to the molecule of interest, the characteristics of the electron spin resonance signal of the paramagnetic molecule change, providing the ratio of bound-to-unbound molecules that leads to the glucose levels with high accuracy.

FIGS. 2A-C show the operational principles of conventional commercial ESR spectrometers (2A) A paramagnetic sample, e.g., a free radical with unpaired electron spin, is placed in a static magnetic field, which orients the magnetic moment of the electron either parallel or anti-parallel with respect to the direction of the field. Electromagnetic radiation, tuned in frequency to the energy difference between the two states, induces transitions that are detected to characterize the sample. (2B) A typical experimental setup for ESR. (2C) Close-up view of the center of the magnet, showing the resonator that focuses the microwave energy onto the sample and improves sensitivity.

DETAILED DESCRIPTION OF THE INVENTION

Figure 3:
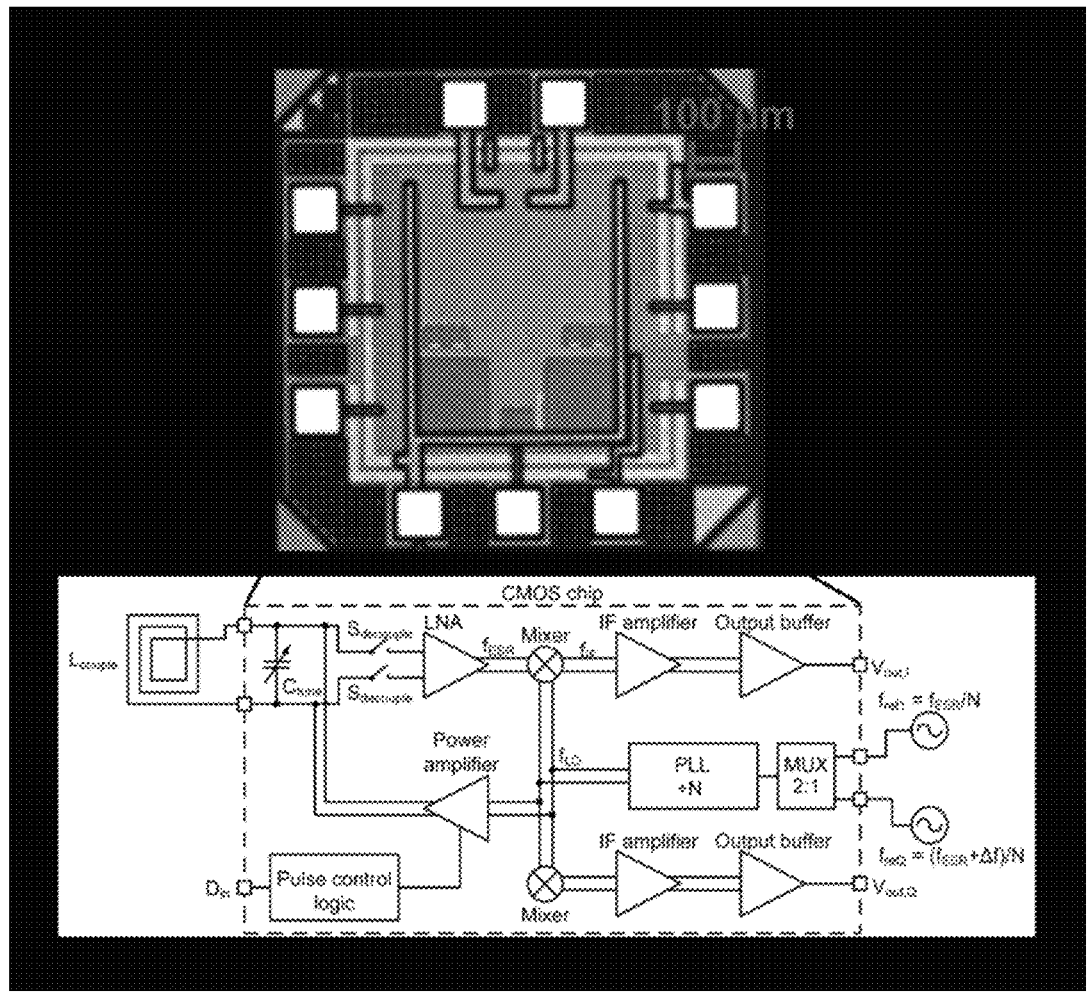
FIG. 3 is a microphotograph and architecture of a broadband NMR spectrometer chip according to an embodiment of the invention.
Figure 4:
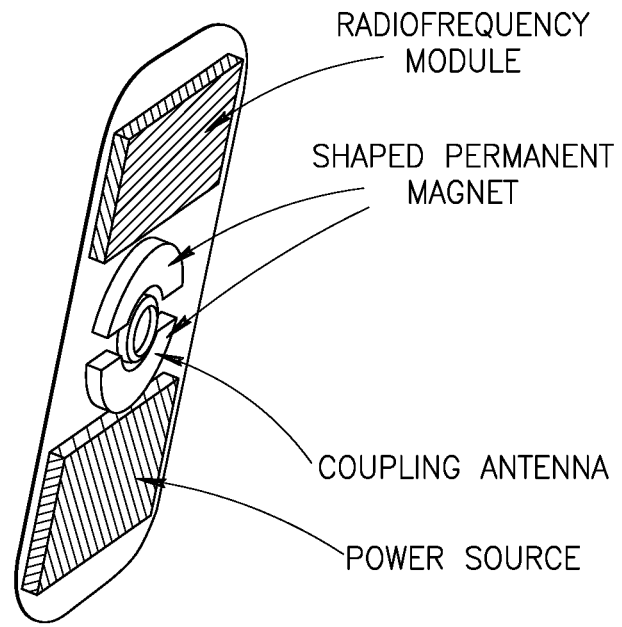
FIG. 4 is an illustration of the unit with compact ESR spectrometer operating with the implant/stent.

The present invention provides, in one embodiment, a compound characterized by a dendritic structure.

In one embodiment, by "dendritic structure" it is meant that a cascade-branched, highly defined, structure which generally comprises a core, a number of generations of ramifications and an external surface.

In one embodiment, the generations of ramifications are composed of repeating structural units, which radially extend outwardly from the core. The external surface of a dendritic structure of a final generation is, typically, composed of the terminal functional groups (also known as "end groups", for example, D, L, or G, as defined below) of the final generation. The first-generation dendritic structure has one to nine (e.g., six) branching moieties and the number of end groups will depend on the number of ramifications of the branching moieties. A second-generation dendritic structure has, e.g., additional branching moieties, and the number of end groups will depend on the number of ramifications of the branching moieties and will be raised accordingly. In one embodiment, the dendritic structure is represented by the general Formula I: $W-[B_1]_n^0-[B_2]_m^1-[B_3]_m^2- \ldots [B_g]_m^{g-1}-[D]^h L^i - G^j$.

In one embodiment, W is a core moiety. In one embodiment, W is a ring core moiety. In one embodiment, W is a ring core moiety of $N_3P_3$. In one embodiment, the compound is a dendrimer. In one embodiment, the compound is a dendrimer comprising a ring core moiety, a paramagnetic (radical) group, a linking moiety and a branching moiety.

In one embodiment, the dendrimer or compound of the invention has a high affinity to an analyte within a biological specimen. In one embodiment, the dendrimer or compound of the invention is used for continuously probing and quantifying an analyte. In one embodiment, the dendrimer or compound of the invention is used for sensitive, accurate, in-vivo measurement of analytes. In one embodiment, component D is a ligand or a binding moiety of analyte G. In one embodiment, the dendrimer or compound of the invention is coupled to kits and devices for performing sensitive, accurate and durable measurements of analytes.

In one embodiment, D comprises a paramagnetic group. In one embodiment, D comprises a spin-trapping group (i.e. TEMPO).

In one embodiment, L is a G-linking moiety.

In one embodiment, G is a species selected from the group consisting: carbohydrate, cholesterol, urea, creatine, and an ion.

In one embodiment, $B_1, B_2, B_3 \ldots B_g$ are each independently a branching moiety, wherein $B_1, B_2, B_3 \ldots B_g$ together form a dendritic structure.

In another embodiment, n is an integer that equals to 1 to 9. In another embodiment, n is an integer that equals to 2 to 8. In another embodiment, n is an integer that equals to 2 to 6. In another embodiment, n is an integer that equals to 4. In another embodiment, n is an integer that equals to 6. In another embodiment, g is an integer that ranges from 1 to 14, representing the number of generations of the dendritic structure. In another embodiment, g is an integer that ranges from 1 to 10, representing the number of generations of the dendritic structure. In another embodiment, g is an integer that ranges from 2 to 8, representing the number of generations of the dendritic structure. In another embodiment, g is an integer that ranges from 1 to 3. In another embodiment, g is an integer that ranges from 1 to 2. In another embodiment, m is an integer that equals 0 to 6 representing, in each occurrence, the ramification number of each generation. In another embodiment, m is an integer that equals 1 to 6. In another embodiment, m is an integer that equals 1 to 4. In another embodiment, m is an integer that equals 1, 2, or 3. In another embodiment, h is an integer that ranges from 1 to $n \times m^1 \times m^2 \times \ldots m^{g-1}$, representing the total numbers of D in the dendritic structure. In another embodiment, i is an integer that ranges from 1 to h, representing the total numbers of L in the dendritic structure. In another embodiment, j is an integer that ranges from 0 to i, representing the total numbers of G in the dendritic structure. In another embodiment, j is greater than zero. In another embodiment, j is greater than one.

Herein, "ramification number" refers to the number of branches (also referred to "branching moieties") extended outwardly from a branch of an earlier generation. For example, when the dendritic structure has two generations (g=2), the number of branching moieties extended outwardly from a branch of the first generation is $m^1$, for example, 2. That is, when n is 6 (i.e. there are 6 branching moieties attached to W) h will have the maximum value of 12 (6×2), see scheme in FIG. 5B.

For yet another example, when the dendritic structure has four generations (g=4), the number of branching moieties extended outwardly from the first, second and third generations are $m^1$, $m^2$, and $m^3$, respectively. That is, when n is 6, and e.g., each of $m^1$, $m^2$, and $m^3$ equals 2, h will have the maximum value of 48 (6×2×2×2).

In another embodiment, L (i.e. G-linking moiety) comprises one or more functional groups. In another embodiment, each of the functional groups being independently selected from, without being limited thereto, hydroxyl, chlorine, and amino acid.

In another embodiment, D is a radical. In another embodiment, D is a mono radical. In another embodiment, D is a diradical. In another embodiment, D is a triradical.

In another embodiment, L is a ligand of a body sample. In another embodiment, D is a ligand of a molecule present in a living organ. In another embodiment, L is a ligand of a bodily fluid constituent (such as blood, urine, semen, or saliva). In another embodiment, bodily fluid is expelled bodily fluid. In another embodiment, L has a high affinity to a bodily fluid constituent. In another embodiment, L has a high affinity to a blood constituent. In another embodiment, L has a high affinity to a plasma constituent. In another embodiment, L is a ligand of a carbohydrate. In another embodiment, L is a ligand of glucose. In another embodiment, L is a ligand of an alcohol. In another embodiment, L is a ligand of ethanol. In another embodiment, L is a ligand of a bacterial toxin. In another embodiment, L is a ligand of bacterial or a viral component.

In another embodiment, a radical group is derived from a nitroso group. In another embodiment, a radical group is derived from a perchlorotriphenylmethyl radical. In another embodiment, a radical group comprises a trityl radical. In another embodiment, D comprises a trityl radical. In another embodiment, a radical group or D comprises a perchlorotriphenylmethyl (PTM) radical. In another embodiment, radical group or D comprises a nitroso radical. In another embodiment, a spin-trapping group or D comprises a tetramethylpiperidin-1-yl)oxyl (TEMPO). In another embodiment, a radical group is derived from a Doxil radical. In another embodiment, a radical group is derived from a picrylhydrazyl radical. In another embodiment, a radical group is derived from a Proxil radical. In another embodiment, a radical group is derived from a Galvinoxyl radical. In another embodiment, a radical group is derived from a,3-bisdiphenylene-2-phenylallyl (BDPA) radical. Further non-limiting exemplary radicals are selected from alpha-phenyl N-tertiary-butyl nitrone (PBN), 5,5-dimethyl-pyrroline N-oxide (DMPO), 5-Diisopropoxyphosphoryl-5-methyl-1-pyrroline-N-oxide (DIPPMPO).

In another embodiment, said G-linking moiety comprises a boronic acid moiety. In another embodiment, core moiety comprises a phosphorus-containing ring.

In another embodiment, branching moiety is further attached to a linking moiety. The moiety may link an end of said branching moiety to an additional branching moiety. In another embodiment, the linking moiety comprises an aldehyde. In another embodiment, branching moiety comprises at least one phosphorus atom. In another embodiment, branching moiety comprises 1 to 5 phosphorus atoms. In another embodiment, branching moiety comprises 2 to 4 phosphorus atoms. In another embodiment, branching moiety comprises 1 to 3 phosphorus atoms. In another embodiment, branching moiety comprises 1 phosphorus atom. In another embodiment, branching moiety comprises 2 phosphorus atoms.

In another embodiment, a compound as described herein is a phosphorus dendrimer. In another embodiment, a compound as described herein is a phosphorus dendrimer based on a cyclotriphosphazene core, TEMPO, or PTM radicals. In another embodiment, a compound as described herein is a phosphorus dendrimer based on a cyclotriphosphazene core, TEMPO, or PTM radicals and boronic acid as glucose-receptor moiety.

In another embodiment, the device/kit of the invention selectively recognizes glucose and the ESR signal changes depending on the number of glucose molecules bound to the compound as described herein.

Figure 5:
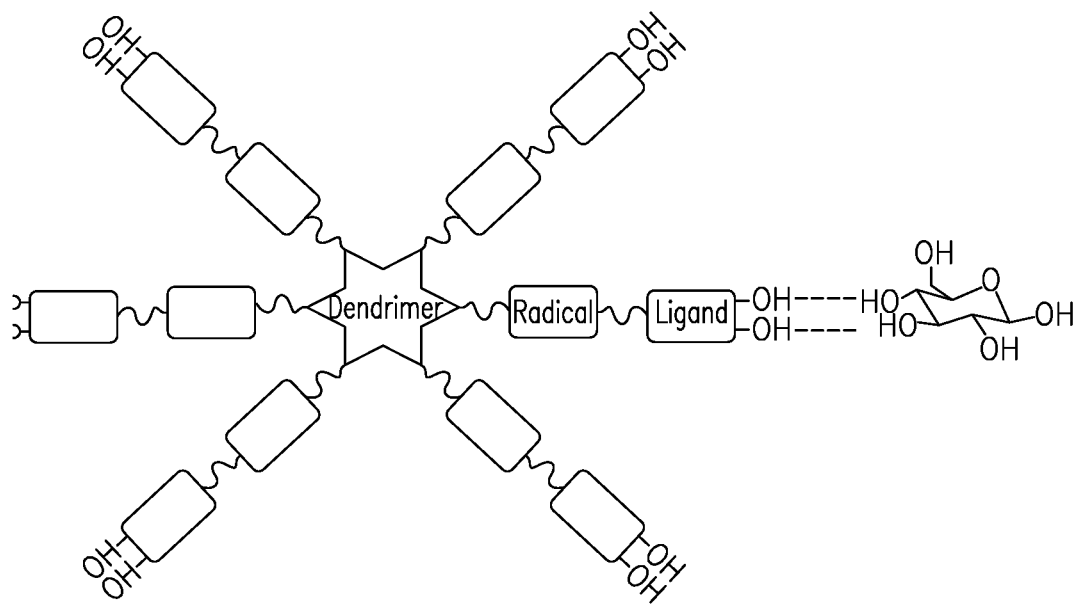
FIGS. 5A-B Are illustrations of some embodiments of the compound-dendrimer of the invention.
Figure 5B:
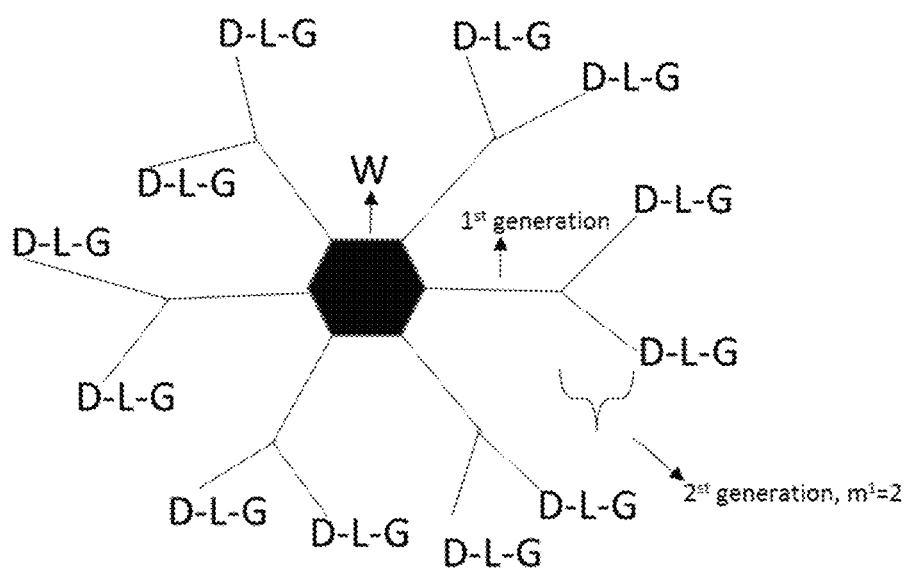

In another embodiment, synthesis of phosphorus-comprising dendrimers involves two synthetic steps: starting from hexachlorocyclotryphosphazene, with p-hydroxybenzaldehyde in basic media, Gc0' is obtained, which in a second step reacts with dichlorophosphonomethylhydrazide to obtain the next generation ending in chlorine (Gc1) that reacts again with p-hydroxybenzaldehyde to obtain the next generation ending in aldehyde (Gc1'), and so on with the following generations. In another embodiment, zero- or first-order dendrimer generations capped by chlorine, are used. In another embodiment, an amino acid as spacer binds both the radical and the analyte (such as glucose) binding molecule to the dendrimer: for example, a TEMPO radical with an acid functional group and a boronic acid derivative functionalized with an amino group (FIG. 5A).

Devices and Kits

In another embodiment, provided herein a device or a kit, comprising: (a) the compound as described herein; and (b) a unit comprising an electron spin resonance spectrometer. An electron spin resonance (ESR) spectrometer is also referred to as "Electron paramagnetic resonance (EPR) spectrometer". In another embodiment, the compound as described herein is coupled to a stent. In another embodiment, the compound as described herein is adhered to a stent. In another embodiment, the compound as described herein coats at least one surface of a stent. In another embodiment, the compound as described herein coats at least one outer-surface of a stent. In another embodiment, the stent is an intra-arterial stent, or in the interstitial tissue.

In another embodiment, provided a device or a kit comprising a resonant radio-frequency coil. In another embodiment, the stent comprises a resonant radio-frequency coil. In another embodiment, provided a device or a kit comprising a microwave pulse antenna. In another embodiment, the stent comprises a microwave pulse antenna. In another embodiment, the compound as described herein is in contact with the antenna, the resonant radio-frequency coil, or both. In another embodiment, the compound coats at least one surface of the antenna. In another embodiment, the compound coats at least one outer-surface of the antenna.

In another embodiment, the electron spin resonance spectrometer is coupled to an electron spin resonance receiver adapted to receive a microwave pulse from the antenna. In another embodiment, the unit comprises an electron spin resonance receiver. In another embodiment, the electron spin resonance receiver is wirelessly connected to the electron spin resonance spectrometer and/or to the antenna. In another embodiment, the electron spin resonance receiver is wirelessly connected to the antenna. In another embodiment, the stent comprises the electron spin resonance receiver. In another embodiment, the electron spin resonance receiver is positioned outside the stent.

In another embodiment, the device comprises the electron spin resonance receiver. In another embodiment, the stent comprises the antenna. In another embodiment, the unit comprises the electron spin resonance spectrometer. In another embodiment, the device is coupled with a pulse spectrometer. Pulse spectrometer may allow to generate pulses with arbitrary shape and phase.

In another embodiment, the unit comprises a magnet. In another embodiment, the electron spin resonance spectrometer is coupled to a magnet. In another embodiment, the unit comprises a magnet. In another embodiment, the electron spin resonance spectrometer is physically connected to a magnet. In another embodiment, the magnet is a static magnet. In another embodiment, the magnet is configured to create a homogenous field at the location of the antenna. In another embodiment, the magnet comprises samarium cobalt.

In another embodiment, the unit, the device or the kit further comprises a power source. In another embodiment, the unit, the device or the kit further comprises a computing unit for calculating and providing data such as concentration or amount of an analyte, based on measurements or based on binding events of the analyte or G to component L.

Methods

In another embodiment, provided herein a method of monitoring an amount or a concentration of a molecule within a composition.

In another embodiment, provided herein a method of monitoring a concentration of a molecule within a composition. In another embodiment, provided herein a method of paramagnetically monitoring an amount of a molecule within a composition. In another embodiment, provided herein a method of paramagnetically monitoring a concentration of a molecule within a composition.

In another embodiment, "paramagnetically monitoring" refers to using ESR for indirectly detecting species that is not paramagnetic. In another embodiment, the monitoring is performed through coupling the species to an ESR-measurable paramagnetic species. In another embodiment, a method as described herein comprises: contacting the compound of the invention with a composition susceptible of comprising a molecule; and employing an electron spin resonance probe for monitoring the amount of the molecule within the composition.

In another embodiment, the composition is a bodily fluid. In another embodiment, the composition comprises a biopsy interstitial tissue. In another embodiment, the composition comprises cells. In another embodiment, the composition comprises a bodily fluid. In another embodiment, the composition comprises blood. In another embodiment, the composition comprises a biological specimen. In another embodiment, the composition comprises an organic molecule. In another embodiment, the composition comprises a protein. In another embodiment, the composition comprises a carbohydrate. In another embodiment, the molecule is selected from the group consisting: an organic molecule, a protein, a carbohydrate, cholesterol, urea, creatine, and an ion. In another embodiment, the molecule is glucose.

In another embodiment, monitoring is in-vivo monitoring. In another embodiment, monitoring is ex-vivo monitoring. In another embodiment, monitoring is in-situ monitoring.

In another embodiment, provided herein a method for in-vivo monitoring an amount and/or a concentration of a molecule within a bodily fluid in a subject, comprising attaching the device or a kit of the invention to a subject, wherein attaching comprises: (a) inserting the compound as described herein into a biological specimen such as a bodily fluid and (b) externally coupling the unit to the subject, thereby monitoring an amount of a molecule within a bodily fluid. In another embodiment, externally coupling the unit to the subject is securing the unit to the subject's cloths. In another embodiment, externally coupling the unit to the subject is externally securing the unit to the subject's arms or legs.

In another embodiment, provided herein a method for monitoring an amount or a concentration of a molecule within a biological specimen, comprising: (a) contacting the compound of the invention with the biological specimen; and (b) coupling the unit as described herein with the molecule, thereby monitoring an amount or a concentration of a molecule within a bodily fluid. In another embodiment, provided herein a method for monitoring an amount or a concentration of a molecule within a biological specimen, comprising: (a) contacting the compound of the invention with the biological specimen, wherein the compound of the invention is coupled an electron spin resonance spectrometer; and (b) coupling the receiver as described herein with the spectrometer, thereby monitoring an amount or a concentration of a molecule within a bodily fluid.

In one embodiment, as provided in FIG. 1 the unit comprising the electron spin resonance spectrometer is placed on a body part such as the arm to detect the signal from a paramagnetic molecule that binds to the molecule of interest (e.g., glucose). In one embodiment, the paramagnetic molecule is embedded in an implantable stent placed in a blood vessel or tissue. In one embodiment, upon binding to the molecule of interest, the characteristics of the electron spin resonance signal of the paramagnetic molecule change, providing the ratio of bound-to-unbound molecules that leads to the glucose levels with high accuracy.

In one embodiment, the stent or implant of the invention comprises a wire or a metal wire coated with a compound of the invention. In one embodiment, the stent or implant of the invention provides an accurate continuous monitoring of small-molecule concentration (such as but not limited to glucose).

In one embodiment, the stent or implant of the invention comprises an implantable radio-frequency coil that is embedded in a stent-like structure inside a tissue or a blood vessel, coated with compound (dendrimer) of the invention. In one embodiment, monitoring as described herein (bound or unbound) is based on electron spin resonance (ESR) signal (see FIG. 2). In one embodiment, electromagnetic waves are used, and can penetrate the skin and the bloodstream thus providing high accuracy spectroscopic data without any other interfering signals. In one embodiment, the stent/implantable device serves both as a scaffold for holding the compound of the invention in a stable manner in the bloodstream, as well as facilitate the coupling of external radio-frequency (RF) radiation required for the ESR measurement into a miniature tuned resonant RF coil that will be an integral part of the stent-like device structure.

In one embodiment, the stent or implant of the invention comprises an implantable RF antenna coated with a compound of the invention. In one embodiment, the implantable RF antenna comprises a memory alloy. In one embodiment, the implantable RF antenna comprises nitinol.

In one embodiment, the magnet provides a static field of ~700 G external to the magnet structure (~5 mm below the magnet surface) with homogeneity of ~0.1% for a region of 0.5 to 20 mm. In one embodiment, the static magnetic field covers a relevant volume in a blood vessel.

In one embodiment, spectrometer is a miniature ESR spectrometer. In one embodiment, spectrometer is within the working range of 2 GHz±20% (corresponding to the static field of 700 G).

What is claimed is:

1. A kit, comprising: (a) a paramagnetic tag; and (b) a unit comprising an electron spin resonance spectrometer; wherein the paramagnetic tag has a dendritic structure, represented by the general Formula I:

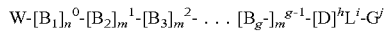

$$W\text{-}[B_1]_n^0\text{-}[B_2]_m^1\text{-}[B_3]_m^2\text{-} \ldots [B_g\text{-}]_m^{g-1}\text{-}[D]^h L^i\text{-}G^j$$

wherein:
W is a ring core moiety;
D comprises a spin-trapping group;
L is a G-linking moiety;
G is a species selected from the group consisting: carbohydrate, cholesterol, urea, creatine, and an ion;
$B_1, B_2, B_3 \ldots B_g$ are each independently a branching moiety, wherein $B_1, B_2, B_3 \ldots B_g$ together form a dendritic structure;
n is an integer that equals to 2 to 6;
g is an integer that ranges from 1 to 10, representing the number of generations of said dendritic structure;
m is an integer that equals 1, 2, or 3 representing, in each occurrence, the ramification number of each generation;
h is an integer that ranges from 1 to $n \times m^1 \times m^2 \times \ldots m^{g-1}$, representing the total numbers of D in said dendritic structure;
i is an integer that ranges from 1 to h, representing the total numbers of L in said dendritic structure, and
j is an integer that ranges from 0 to i, representing the total numbers of G in said dendritic structure.

2. The kit of claim 1, wherein said compound is coupled to an intra-arterial stent.

3. The kit of claim 1, comprising a resonant radio-frequency coil, a microwave pulse antenna, or both.

4. The kit of claim 1, comprising a microwave pulse antenna wherein a surface of said antenna is coated with said compound.

5. The kit of claim 1, wherein said electron spin resonance spectrometer is coupled to an electron spin resonance receiver adapted to receive a microwave pulse from said antenna.

6. The kit of claim 1, wherein said electron spin resonance spectrometer is coupled to a magnet.

7. The kit of claim 1, wherein said D is selected from the group consisting of a trityl radical, a nitroso radical, tetramethylpiperidin-1-yl)oxyl (TEMPO), and a perchlorotriphenylmethyl (PTM) radical; and wherein said core moiety comprises a phosphorus-containing ring.

8. The kit of claim 1, wherein said wherein said phosphorus-containing ring is cyclotriphosphazene; wherein said G-linking moiety comprises a boronic acid moiety; and wherein said branching moiety is further attached to a linking moiety, said linking moiety links an end of said branching moiety to an additional branching moiety; and wherein: n is 6, g is 1 or 2, j is not 0.

9. A method for in-vivo, in-situ or both monitoring an amount of a molecule within a bodily fluid or interstitial tissue in a subject, comprising attaching a kit of claim 1 to said subject, wherein said attaching comprises: (a) inserting said paramagnetic tag into said bodily fluid; and (b) externally coupling said unit to a body surface of said subject, thereby monitoring an amount of the molecule within said bodily fluid.

* * * * *